(12) United States Patent
Friedman et al.

(10) Patent No.: US 6,322,992 B1
(45) Date of Patent: Nov. 27, 2001

(54) METHOD FOR THE DETERMINATION OF A SPECIFIC BINDING LIGAND USING A VANADIUM BROMOPEROXIDASE AS A SIGNAL-GENERATING ENZYME

(75) Inventors: Alan Eric Friedman; Thomas Robert Kissel, both of Rochester; Sarah Fingar Groulx, Ontario; Martha Miller Kopcienski, Spencerport, all of NY (US)

(73) Assignee: Johnson & Johnson Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 08/953,071

(22) Filed: Oct. 17, 1997

Related U.S. Application Data

(63) Continuation of application No. 08/523,042, filed on Sep. 1, 1995, now abandoned.

(51) Int. Cl.[7] ................................................. G01N 33/53
(52) U.S. Cl. ............................ 435/7.92; 422/52; 422/56; 435/7.1; 435/7.9; 435/7.93; 435/7.94; 435/7.95; 435/28; 435/287.7; 435/287.8; 436/518; 436/524; 436/541; 436/805; 436/810
(58) Field of Search ....................... 422/52, 56; 435/7.1, 435/7.9, 7.92, 7.93, 7.94, 7.95, 28, 287.7, 287.8; 436/518, 524, 541, 805, 810

(56) References Cited

U.S. PATENT DOCUMENTS

| | | |
|---|---|---|
| 3,992,158 | 11/1976 | Przybylowicz et al. |
| 4,250,189 * | 2/1981 | Hydes et al. |
| 4,258,001 | 3/1981 | Pierce et al. |
| 4,292,272 | 9/1981 | Kitajima et al. |
| 4,301,139 * | 11/1981 | Feingers et al. .............. 424/1 |
| 4,361,537 * | 11/1982 | Deutsch et al. ............. 422/56 |
| 4,430,436 | 2/1984 | Koyama et al. |
| 4,670,381 | 6/1987 | Frickey et al. |
| 4,806,311 * | 2/1989 | Greenquist ................. 422/56 |
| 4,806,312 * | 2/1989 | Greenquist ................. 422/56 |
| 4,828,978 | 5/1989 | Warren, III et al. |
| 4,997,772 | 3/1991 | Sutton et al. |
| 5,106,732 | 4/1992 | Kondo et al. |
| 5,147,777 | 9/1992 | Sutton et al. |
| 5,177,023 | 1/1993 | Sutton et al. |
| 5,324,835 | 6/1994 | Yamaguchi . |
| 5,372,931 | 12/1994 | Friedman et al. |
| 5,372,932 | 12/1994 | Friedman et al. |
| 5,460,777 * | 10/1995 | Kitajima et al. ............ 422/56 |
| 5,556,758 | 9/1996 | Allen ............................. 435/7.9 |

FOREIGN PATENT DOCUMENTS

| | | | |
|---|---|---|---|
| 91310875.9 | 11/1991 | (EP) | ............. G01N/33/533 |
| 81108364.1 | 10/1981 | (EP) | ............. G01N/33/54 |
| 81108365.8 | 10/1981 | (EP) | ............. G01N/33/54 |
| 82/02601 | 8/1982 | (WO) . | |

OTHER PUBLICATIONS

Braman, Robert et al Nanogram Nitrite and Nitrate Determination in Environmental and Biological Materials by Vanadium (III) Reduction with Chemiluminescence Detection, Anal. Chem., pp. 2715–2718, 1989.*

Itoh, Nobuya et al. Purification and Characterization of a Novel Metal–Containing nonheme bromoperoxidase from *Pseudomonas putida*, Biochimica et Biophysica Acta, pp. 208–216, 1994.* de Boer, E et al Vanadium Containing Bromoperoxidase: An Example of an Oxidoreductase with High Operational Stability in Aqueous and Organic Media, Biotechnology and Bioengineering, vol. 30, pp. 607–610, 1987.*

Tschirret–Guth, Richard et al. Evidence for Organic Substrate Binding to Vanadium Bromoperoxidase, J. Am. Chem. Soc. vol. 116, pp 411–412, 1994.*

Vollenbroek, E.G.M. et al Vanadium chloroperoxidases occur widely in nature, Biochemical Society Transactions, vol. 23, 1995.*

Butler et al. (1993), "Marine Haloperoxidase", Chem. Rev., 93, pp. 1937–1944.

Yoshitake et al. (1979), "Conjugation of Glucose Oxidase from *Aspergillus niger* and Rabbit Antibodies using N–Hydroxysuccinimide Ester of N–(4–Carboxycyclohexylmethyl)–Maleimide", Eur. J. Biochem. 101, pp. 396–399.

* cited by examiner

*Primary Examiner*—Long V. Le
*Assistant Examiner*—Bao-Thuy L. Nguyen
(74) *Attorney, Agent, or Firm*—Todd F. Volyn; James Harrington; Charles LiMuti

(57) ABSTRACT

An analytical element can be used to sensitively and rapidly detect a wide variety of specific binding ligands in either a competitive or sandwich assay format. The assays are carried out using a vanadium bromoperoxidase-labeled immunoreactant and a chemiluminescent signal-providing wash composition which comprises a 2,3-dihydro-1,4-phthalazinedione derivative; a halogen, pseudohalogen, halogen-providing source or pseudohalogen-providing source; and a peroxide or a peroxide-generating reagent composition.

30 Claims, 5 Drawing Sheets

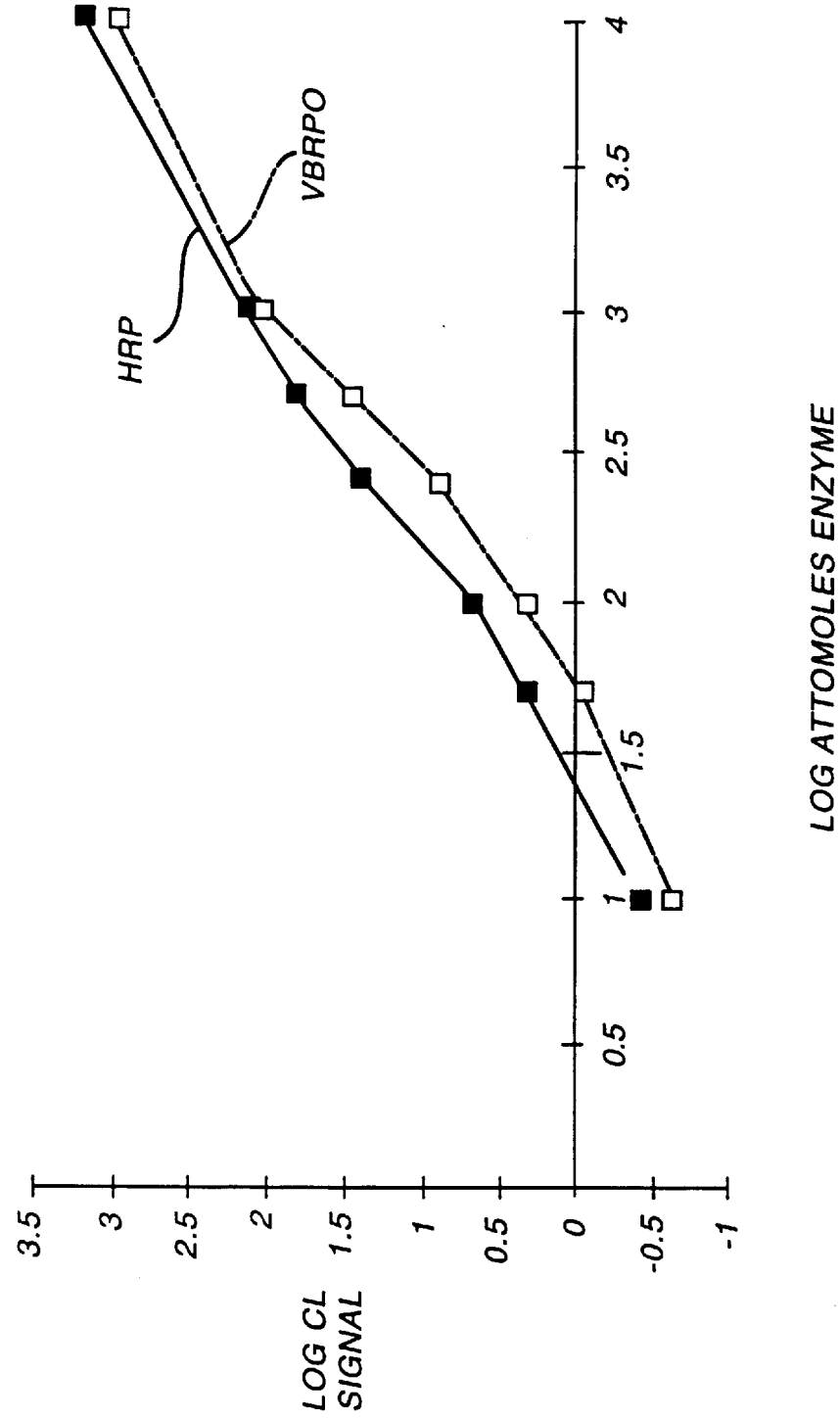

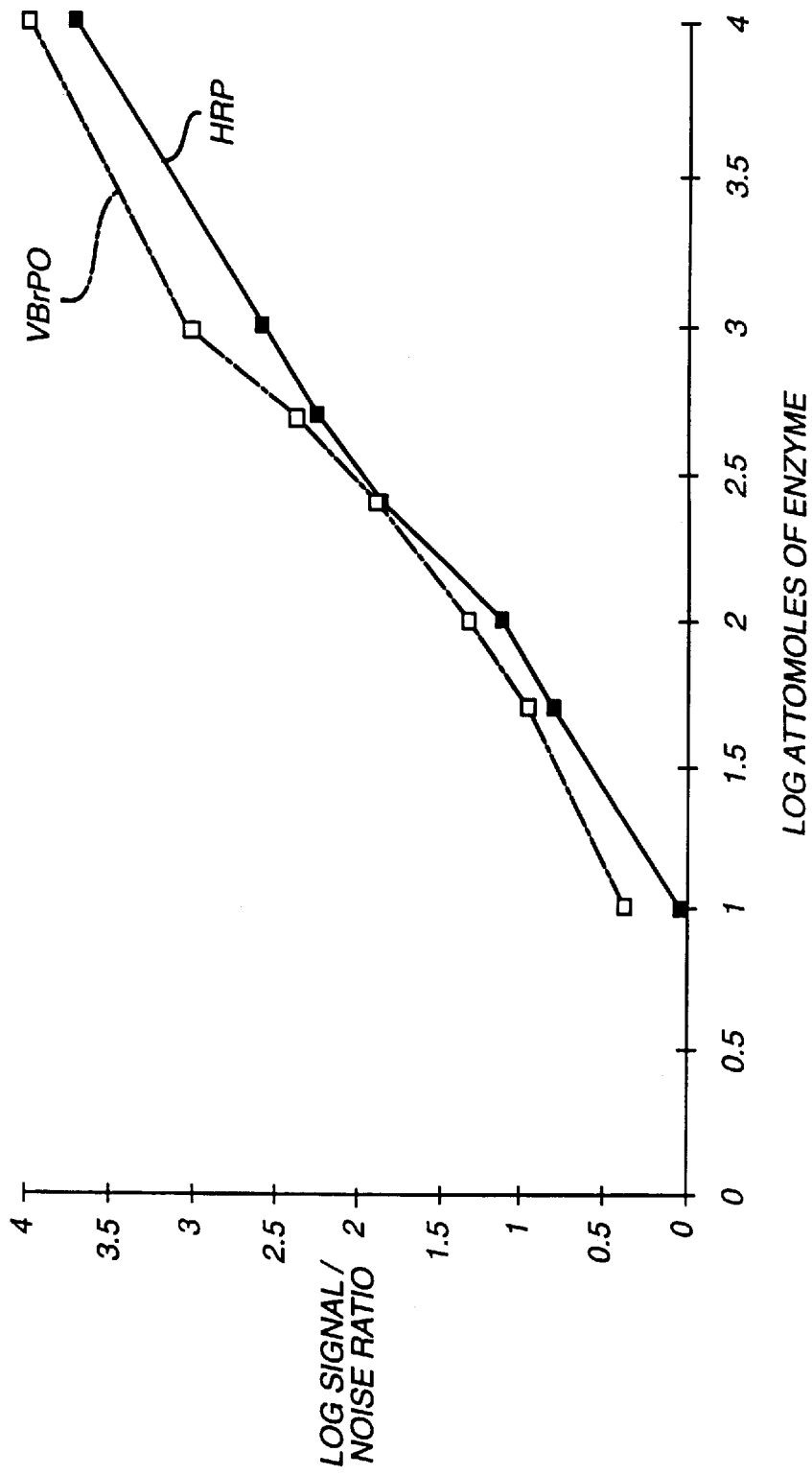
FIG. 2 VBrPO VS HRP ON A COATING: LOG SIGNAL / NOISE RATIO

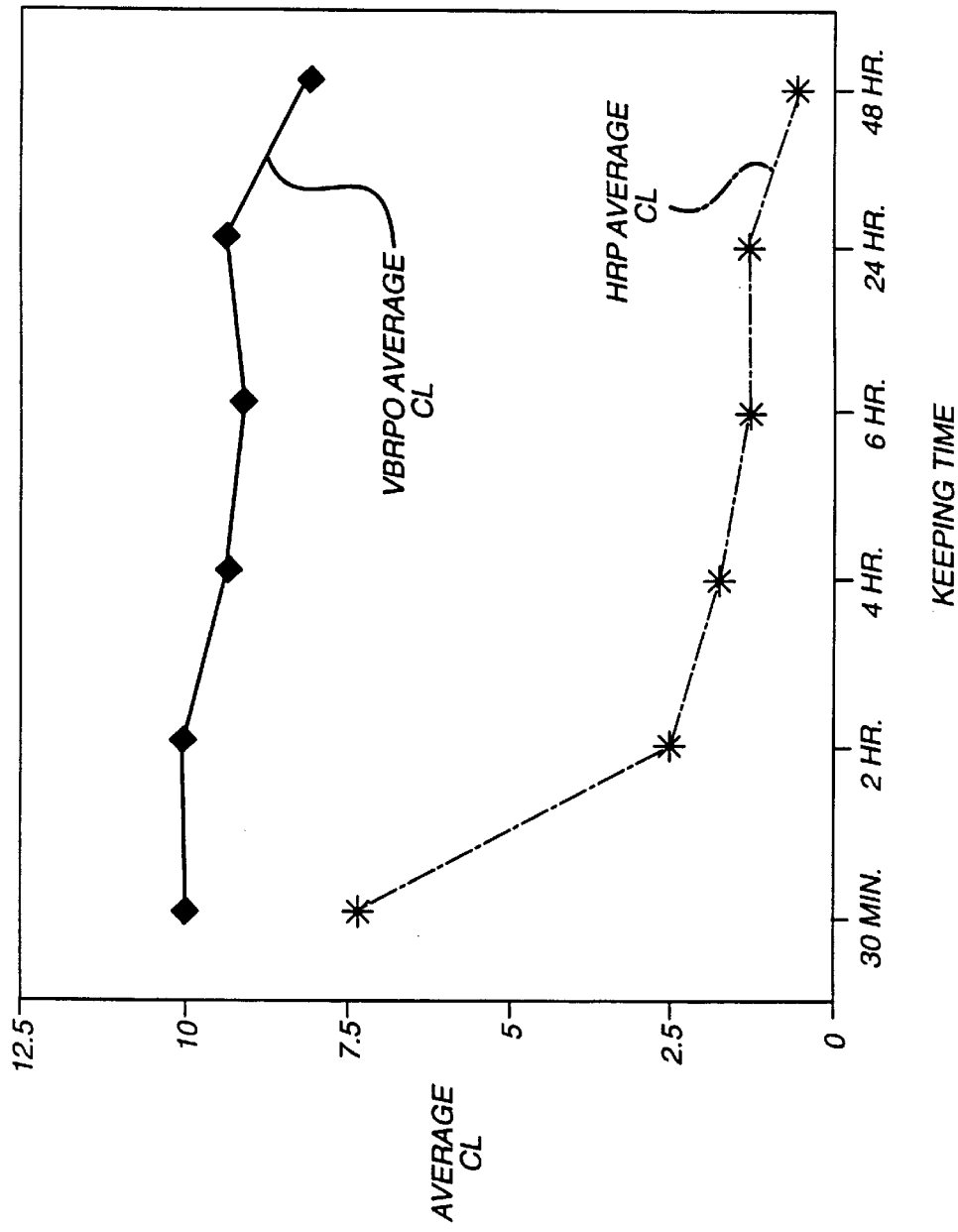

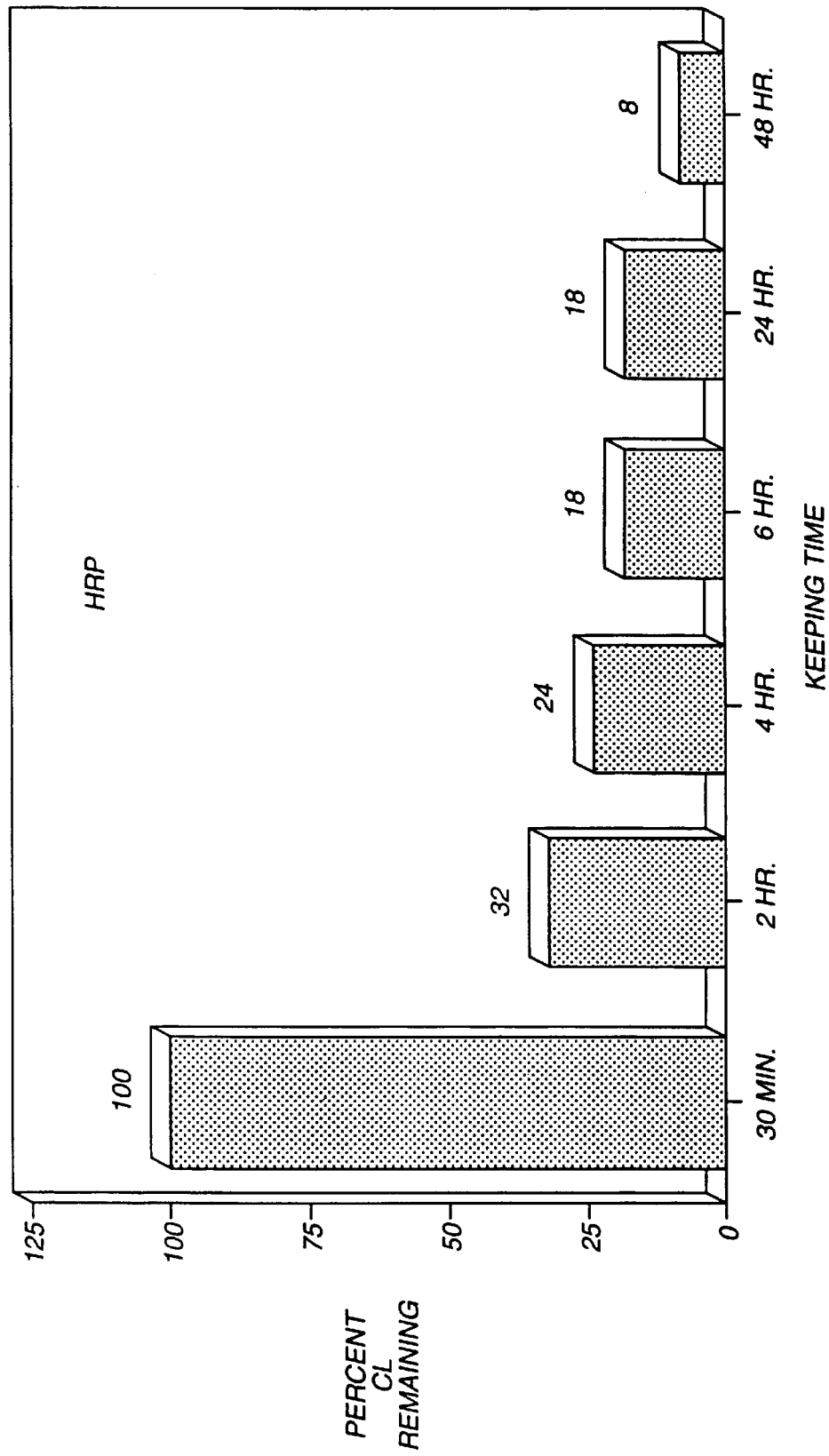

METHOD FOR THE DETERMINATION OF A SPECIFIC BINDING LIGAND USING A VANADIUM BROMOPEROXIDASE AS A SIGNAL-GENERATING ENZYME

This is a continuation of application Ser. No. 08/523,042, filed Sep. 1, 1995, now abandoned.

FIELD OF THE INVENTION

The present invention relates to analytical elements and methods for using the same to detect specific binding ligands in fluid samples. More particularly, the present invention relates to the use of a vanadium bromoperoxidase as a signal-generating enzyme in such analytical elements.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of proteins, hormones, drugs, viruses, microorganisms, narcotics and steroids must be determined rapidly and accurately for effective research, diagnosis and treatment.

A wide variety of analytical methods have been developed in recent decades to detect the noted substances. The methods have become highly reliable and in some instances, suitable for automation, as well as suitable for use in kit form. Most of such methods rely on what are known in the art as "specific binding reactions" between a substance to be detected (identified herein as a "specific binding ligand" or "ligand") and a corresponding "receptor" which recognizes and reacts with the ligand specifically. Most known specific binding reactions are between immunoreactants (in "immunoassays"), such as antibodies with antigens or antibodies with haptens, but others are also known such as avidin with biotin.

In general, immunoassays can provide a qualitative and/or quantitative determination of the presence or absence (or quantity) of a specific antigen, antibody or antigen-antibody complex. In one form of immunoassay, known as a "competitive binding immunoassay", a labeled analog of the ligand to be determined is placed in competition with a fixed amount of an appropriate antibody which can react with both the ligand and the ligand analog. The label on the analog can be appropriately detected in its "free" or complexed (that is, reacted) form. Such detection will then tell the user how much ligand is in the sample being tested.

In an alternative immunoassay format known as a "sandwich" immunoassay or immunometric assay, the ligand is contacted with two or more receptor molecules which bind to the ligand at different epitopic sites. One receptor is appropriately labeled and the other is either immobilized on a solid substrate, or is capable of being immobilized thereon. The amount of ligand is directly proportional to the amount of bound complex among the ligand and the two receptors.

Immunoassays have been traditionally carried out in solution, or in test devices where fluids are removed in some fashion from the reagents participating in the assay. Although solution techniques have enjoyed broad acceptance in this area, they typically require analyzer equipment often having intricate solution handling and transport capabilities. Moreover, the analytical equipment used in such assays can involve complex liquid handling, and may require skilled personnel, both for operation and the precise cleaning that may be needed to avoid sample to sample contamination.

An alternative to solution chemistry is the use of dry analytical elements. It should be understood that not all aqueous solutions can be employed in dry analytical elements because of interference from coating agents, binders, and other reagents necessary to maintain structural integrity in said elements. Also, a multiplicity of scientific disciplines are often required in successful element construction. Moreover, dry analytical elements must use compartmentalization to segregate incompatible components; such is not the case in solution chemistry where separate liquid storage and successive liquid additions can be employed.

Dry analytical elements and their use for immunoassays are described in numerous publications, including U.S. Pat. No. 4,258,001 to Pierce et al., U.S. Pat. No. 4,670,381 to Frickey et al., WO 82/2601 (published Aug. 5, 1982), European Patent Application No. 051 183 (published May 12, 1982) and European Patent Application No. 066 648 (published Dec. 15, 1982).

Improved dry analytical elements and their use in immunoassays are described in copending and coassigned application, U.S. Ser. No. 938,460, filed Aug. 31, 1992 to Belly et al. in which enzyme labels are utilized for detection. Horseradish peroxidase is the preferred enzyme label disclosed in the application of Belly et al. Such elements allow for the detection of analytes present in very low concentrations using a particular washing technique to separate unbound reactants from bound (or complexed) immunoreactants.

In the immunoassays carried out in the dry analytical elements using peroxidase as the label, the stability of the peroxidase is highly important since any change in its concentration critically affects assay sensitivity. In the assays described in U.S. Pat. No. 5,372,932 to Friedman et al., 4'-hydroxy or 4'-alkoxyarylacetamides are used as agents to enhance the stability of the enzyme or enzyme label in a dry analytical element. Although these agents have resulted in improved stability, it has been observed that the stability of the peroxidase label is still less than desirable in dry analytical elements.

Recently, Butler and Walker have described a family of vanadium bromoperoxidases (VBrPO) extracted from aquatic and marine algae and some from terrestrial lichens and fungi that, in the presence of hydrogen peroxide and bromide anion, catalytically produce activated bromine species which are potent oxidants. (See, Butler et al., *Chem. Revs.*, 93, pp. 1937–1944, 1993 and references cited therein).

One of the problems with most haloperoxidases is that their pH optima are generally in the lower pH range, i.e., 3–5. This presents a problem with prior art analytical elements which depend upon a peroxy anion; peroxides typically have a pKa of about 11.5. The vanadium bromoperoxidases work effectively in a pH range of about 6–10.

Although the analytical elements and methods disclosed in the prior art show enhanced assay sensitivity and stability, there is still a need for further improvements in this field. For example, there is still a need for providing a simpler analytical element which does not require the use of stabilizing agents as described in U.S. Pat. No. 5,372,932 to Friedman et al. Furthermore, there still is a need to provide an element which has improved enzyme stability and more sensitivity than the known prior art systems.

SUMMARY OF THE INVENTION

The problems identified above in regard to prior art dry analytical elements and immunoassays have been overcome by the present invention by utilizing an analytical element which comprises, in at least one of its zones, a vanadium bromoperoxidase-labeled immunoreactant.

More specifically, the present invention relates to an analytical element useful for the determination of a specific binding ligand comprising:

(i) a porous spreading zone, (ii) one or more additional zones which are in fluid contact with the porous spreading zone, and (iii) optionally, an absorbent material in fluid contact with the above zones, wherein said element, in at least one of the zones, contains a vanadium bromoperoxidase-labeled immunoreactant which is capable of specifically reacting with either a specific binding ligand of interest or its receptor.

The present invention also provides a method for the determination of a specific binding ligand using the above immunoassay analytical element and comprising:

(A) contacting a fluid sample suspected of containing the specific binding ligand with said analytical element;

(B) contacting said analytical element with a wash composition comprising:

(a) a chemiluminescent signal-generating reagent which provides a signal in response to the catalytic activity of a vanadium bromoperoxidase, said signal-generating reagent is a 2,3-dihydro-1,4-phthalazinedione derivative;

(b) a halogen, pseudohalogen, halogen-providing source or pseudohalogen-providing source; and (c) a peroxide or peroxide-generating reagent composition; and (C) detecting either the unreacted or reacted form of the vanadium bromoperoxidase-labeled immunoreactant as a measure of the specific binding ligand of interest.

The present invention provides a highly sensitive and stable composition for use in dry analytical elements. The element of the instant invention is useful for determining a wide variety of specific binding ligands, but it is particularly useful for the determination of ligands at low concentrations. The advantages of enzyme stability and enhanced detection are achieved by incorporating a vanadium bromoperoxidase-labeled immunoreactant into the element.

BRIEF DESCRIPTION OF THE DRAWINGS

FIG. 1 is a graphical representation of the chemiluminescent signal obtained using an element of the present invention which contains a vanadium bromoperoxidase signal-generating enzyme as one of its components and a control element which contains horseradish peroxidase (HRP) as the signal-generating enzyme, and 3'-chloro-4'-hydroxyacetanilide as an enhancer contained in the wash composition as described in Example 1 of U.S. Pat. No. 5,372,931 to Friedman et al.

FIG. 2 is a graphical representation of the signal-to-noise response obtained using an element of the present invention which contains a vanadium bromoperoxidase signal-generating enzyme as one of its components and a control element which contains horseradish peroxidase (HRP) as the signal-generating enzyme, and 3'-chloro-4'-hydroxyacetanilide as an enhancer contained in the wash composition as described in Example 1 of U.S. Pat. No. 5,372,931 to Friedman et al.

FIG. 3 is a graphical representation of the stability of a spotted enzyme assay using an element of the present invention which contains a vanadium bromoperoxidase signal-generating enzyme and a control element which contains horseradish peroxidase as the signal-generating enzyme.

DETAILED DESCRIPTION OF THE INVENTION

Figure 4B:
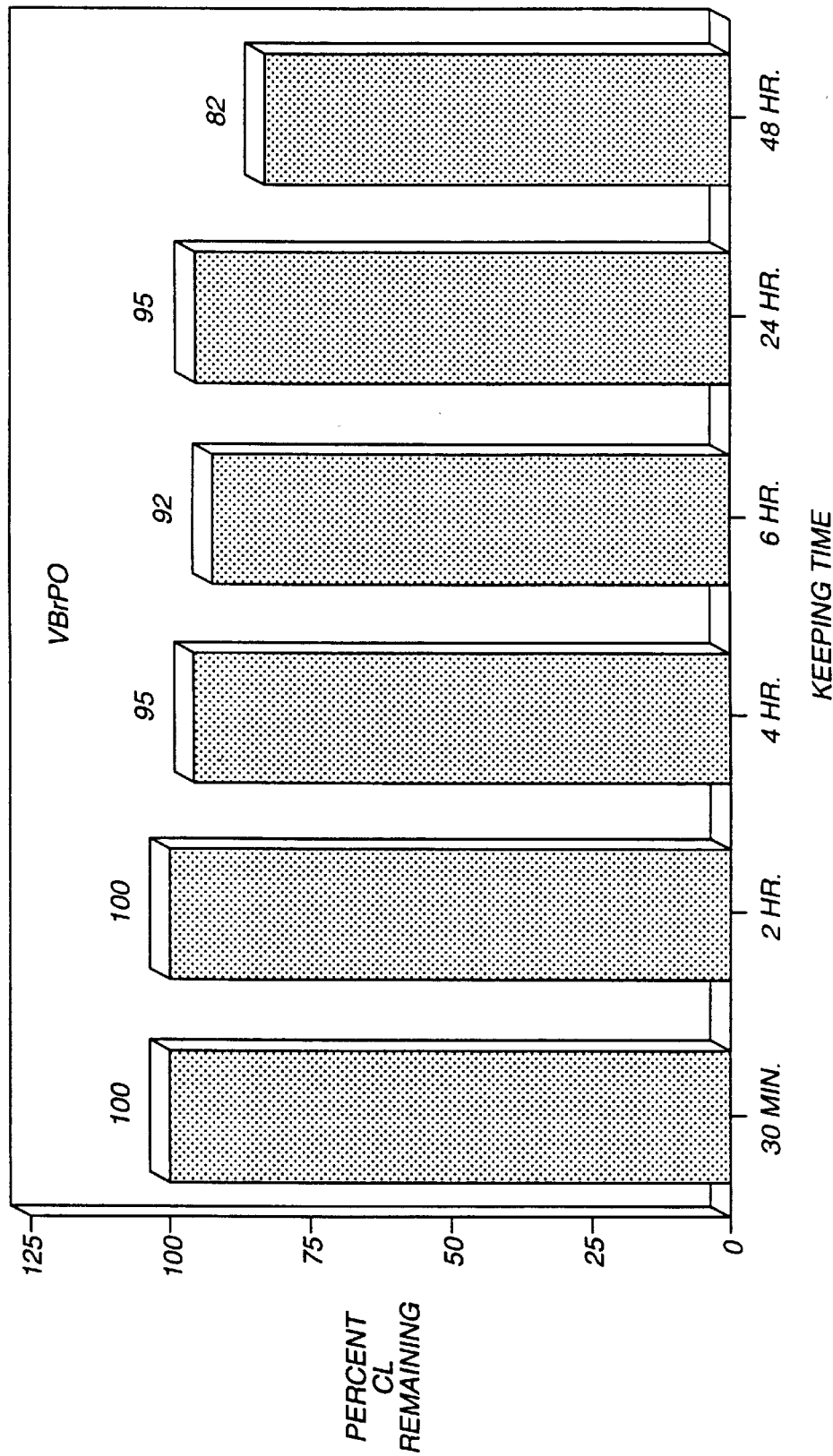
FIGS. 4(a) and (b) are bar graphs depicting the percent of chemiluminescent signal remaining after room temperature storage at various times using an element of the present invention which contains a vanadium bromoperoxidase signal-generating enzyme and a control element which contains horseradish peroxidase (HRP) as the signal-generating enzyme.

The method of the present invention is a specific binding assay, such as an immunoassay, which can be either competitive binding or immunometric as those terms are known in the art. The analyte of interest to be determined is a specific binding ligand, a labeled ligand, a labeled ligand analog, or a receptor thereof.

The present invention is used advantageously to determine low concentrations of ligands in various aqueous liquids, such as human and animal biological fluids, foods, industrial or municipal effluents, and other fluids commonly tested in this manner. Biological fluids which can be tested include, but are not limited to, whole blood, serum, plasma, urine, spinal fluid, lacrimal fluid, synovial fluid, lymphatic fluid, suspensions of tissues or plaque, gingival fluid, vaginal fluid, cranial fluid and other fluids readily apparent to one skilled in the art.

Ligands which can be determined include, but are not limited to, peptides, polypeptides, proteins (such as enzymes, antibodies, lipoproteins and glycoproteins), drugs, narcotics, steroids, toxins and saccharides (such as polysaccharides). Specific binding ligands of particular interest include digoxin, phenytoin, phenobarbital, theophylline, C-reactive protein, human chorionic gonadotropin, thyroid stimulating hormone, a thyronine derivative (such as thyroxine and triiodothyronine), creatine kinase-MB, carbamazepine, gentamicin, tobramycin or vancomycin. The present invention is most useful in the determination of digoxin, phenytoin, phenobarbital and C-reactive protein.

The present invention is carried out using an analytical element comprising a porous spreading zone, usually a coated layer which has suitable porosity for accommodating a test sample (for example 1 to 50 µl), diluted or undiluted. The element of the present invention is assembled using techniques that are well known in the art. Preferably, the porous spreading zone is isotropically porous, which property is provided by interconnected spaces among the particles, fibers or other physical components of the zone. By isotropically porous is meant that fluids are uniformly spread throughout the zone. Useful materials for such zones are water-insoluble and maintain their structural integrity during the assay. Conventional materials and means for assembling the element are described, for example, in U.S. Pat. No. 3,992,158 to Przybylowicz et al., U.S. Pat. No. 4,258,001 to Pierce et al., U.S. Pat. No. 4,292,272 to Kitazima et al. and U.S. Pat. No. 4,430,436 to Koyama et al., the contents of which are incorporated herein by reference. The preferred porous spreading zones are prepared from organopolymeric particles and a polymeric adhesive in a coherent, three-dimensional structure, as described in U.S. Pat. No. 4,258,001 to Pierce et al.

There are one or more additional zones in the element, all of which are in fluid contact with the porous spreading zone.

It should be understood that the term "fluid contact" is used herein to denote that fluids can readily move from one zone to another. Such additional zones, preferably coated polymer layers, include subbing, reagent, and radiation blocking zones and are composed of one or more hydrophilic binder materials as are known in the art, such as gelatin, acrylamide polymers and vinylpyrrolidone polymers. Some zones may be water-insoluble while others may be water-soluble.

The zones of the element of the present invention can be self-supporting, but preferably, these zones are disposed on a suitable dimensionally stable, chemically inert support. Preferably, the support is nonporous and transparent to electromagnetic radiation. A support of choice should be compatible with the intended mode of detection (for example, transmission or reflectance spectroscopy). Useful support materials include, but are not limited to, paper, metal foils, polystyrenes, polyesters, polycarbonates and cellulose esters.

Optionally, the element comprises an absorbent material in fluid contact with the zones of the element of the instant invention. Absorbent materials as used in this invention provide overall added liquid capacity to the element providing a reservoir for the wash fluid used in the method of this invention. Suitable absorbent materials comprise, but are not limited to, glass microfibers, papers, sponges, fabrics, plastics and the like, so long as the material is capable of absorbing a liquid.

In a preferred embodiment, an annular section of the absorbent material is placed on the spreading zone permitting access of the spreading zone to sample and wash.

In at least one of the zones of the element of this invention is a vanadium bromoperoxidase-labeled immunoreactant which is capable of specifically reacting with either the specific binding ligand of interest or its receptor. In competitive binding immunoassays, the labeled immunoreactant is usually a labeled analog of the specific binding ligand. In sandwich assays, the labeled immunoreactant can be a labeled receptor for the ligand, or it can be a labeled molecule which specifically binds to the receptor (such as a labeled anti-antibody).

Such labeled immunoreactant can be prepared using any of a number of known procedures including that described by Yoshitake et al. *Eur. J. Biochem.*, 101, 395, 1979 and in U.S. Pat. No. 5,106,732 to Kondo et al.

As used herein, "vanadium bromoperoxidase" is meant to be any vanadium haloperoxidative substance (enzymatic or otherwise) which catalyzes the oxidation of a substance such as luminol to produce an appropriate chemiluminescent signal. Specific examples of proteinaceous vanadium bromoperoxidase sources that may be employed in the present invention can be found in Butler et al., *Chem. Revs.*, 93, pp. 1937–1944, (1993) and include, but are not limited to, those obtained from *Ascophyllum nodosum, Ceramirum rubrum, Laminaria saccharina, Fucus distichus, Corallina pilulifera, Corallina officinalis, Macrocystis pyrifera* and the like. Procedures for isolation of vanadium bromoperoxidases may be found within the aforementioned Butler et al. reference. Of these proteinaceous vanadium bromoperoxidase sources, *Ascophyllum nodosum* is particularly preferred.

As stated hereinabove, by incorporating a vanadium bromoperoxidase into the dry analytic element, the element of the instant invention quite unexpectedly exhibits improved enzyme stability and enhanced detection without the need of adding enhancers, such as described in U.S. Pat. No. 5,372,931 to Friedman et al., into the element.

The amount of vanadium-bromoperoxidase-labeled immunoreactant can vary widely due to the amount of the other components used in the reaction and the suspected amount of analyte in the test sample. Generally, the amount present in the element is at least about 0.01 $\mu g/m^2$, with the preferred range being from about 0.1 to about 100 $\mu g/m^2$.

The element of the present invention, optionally, may contain an unlabeled immunoreactant which is capable of specifically reacting with either the specific binding ligand of interest or its receptor. In competitive binding immunoassays, this immunoreactant is generally a receptor (such as an antibody) to the ligand. In sandwich immunoassays, the unlabeled immunoreactant can be a receptor for the ligand, or a binding molecule for the receptor. In preferred embodiment, the immunoreactant is an antibody specific to the ligand.

When present, the unlabeled immunoreactant is located in any zone of the element, except it is generally not located in the same zone as the vanadium bromoperoxidase-labeled immunoreactant. Thus, those two components of the element are kept separated in some fashion until the assay has begun. These components may be separated by locating them in different zones of the element, or they may be in the same zone, but one is encapsulated with a material that releases the immunoreactant when the assay is begun. Preferably, the immunoreactants are kept in separate zones or layers.

It is also preferred that the unlabeled immunoreactants are immobilized on suitable particles that are dispersed throughout a zone of the element. Such particles can be composed of any suitable material including, but not limited to, glass, iron oxides, ceramics, organic synthetic or naturally occurring polymers, and have an average particle size of from about 0.01 to about 10 $\mu m$. Preferably, the particles are prepared from synthetic polymers and have suitable surface groups for adsorption or covalent attachment of the immunoreactant molecules. A wide variety of such materials are known in the art such as those described in U.S. Pat. No. 4,828,978 to Warren et al., U.S. Pat. No. 4,997,772 to Sutton et al., U.S. Pat. No. 5,147,777 to Sutton et al. or U.S. Pat. No. 5,177,023 to Sutton et al., and references identified therein.

Particularly useful polymeric particles are those prepared from ethylenically unsaturated polymerizable monomers having reactive carboxy, 2-substituted ethylsulfonyl or vinylsulfonyl groups, particularly as described in the Sutton et al. patents referenced in the preceding paragraph.

In a preferred embodiment of this invention, a multilayer analytical element for the determination of a specific binding ligand is provided. Specifically, the multilayer element comprises a nonporous support having thereon, in fluid contact:

a first reagent or buffer layer, a subbing layer comprising an unlabeled immunoreactant capable of reacting with either a specific binding ligand of interest or its receptor, a porous spreading layer containing uniformly distributed, a vanadium bromoperoxidase-labeled immunoreactant which is capable of reacting with the specific binding ligand of interest or its receptor.

The multilayer element of the present invention may optionally contain an absorbent material which is in fluid contact with one of the aforementioned zones.

In a more preferred embodiment, the vanadium bromoperoxidase-labeled immunoreactant is localized in the top portion of the porous spreading layer by using manufacturing techniques such as, but not limited to, ink jet deposition, spray coat deposition, and gravure deposition as is well known to those skilled in the art.

The elements of this invention can include a variety of additives in appropriate zones as are known in the art to aid in manufacture, fluid spreading, absorbance of unwanted radiation and receptor stability.

The element of the present invention can be prepared using conventional coating procedures and equipment as are described in the prior art (including gravure, curtain, hopper and other coating techniques). The elements can be configured in a variety of forms, including elongated tapes of any desired width, sheets, slides or chips. Further, the method of this invention can be manual or automated using appropriate analytical equipment and procedures. Generally, the method includes contacting the reagents in the element by spotting a test sample (for example, 1 to 50 µl) on the porous spreading zone. The movement of fluid within the element effectively mixes the reagents for the reactions to take place.

After sample application, the element is exposed to any conditioning, such as incubation, heating or other procedure, that may be desirable to quicken or otherwise facilitate forming the appropriate specific binding complexes in the various zones of the element. While in some instances, a suitable signal can be obtained without effective separation of the reacted and unreacted forms of the vanadium bromoperoxidase-labeled immunoreactant, it is preferred that the forms be separated within a zone of the element, as is typical in what are known as heterogeneous immunoassays. Thus, a signal can be better read in a defined region of the zone.

Applying a wash solution (from about 5 to about 200 µl) to the element is the preferred procedure for effecting this separation. The wash solution can be applied in any suitable manner known in the art, but preferably, it is applied at a continuous metered rate, for example of up to 10 µl/sec and most preferably, at about 1 µl/sec. However, any rate and method of wash solution application can be used as long as the porous spreading zone readily absorbs the fluid during application as is readily provided by using the aforementioned absorbent material in the element.

The wash solution can comprise multiple fluid compositions applied sequentially, but at least one of the fluids must comprise the signal-generating composition as described hereinbelow. Alternatively, a surfactant can also be used in any of the wash solutions.

The wash solution employed in the method of the present invention is an analytical composition for providing a chemiluminescent signal having a pH of from about 6.5 to about 10, said composition comprising:

(a) a chemiluminescent signal-generating reagent which provides a signal in response to the catalytic activity of a vanadium bromoperoxidase, wherein the signal-generating reagent is a 2,3-dihydro-1,4-phthalazinedione derivative;

(b) a halogen, pseudohalogen, halogen-providing source or pseudohalogen-providing source; and (c) a peroxide or peroxide-generating reagent composition.

As indicated above, the signal-providing composition employed in the instant invention contains, as one of its components, a 2,3-dihydro-1,4-phthalazinedione derivative (identified herein as "DPD"). Any free or conjugated DPD that can be converted to an excited state in a chemiluminescent reaction and subsequently returns to a non-excited state with the emission of light, is useful in the practice of this invention. A considerable number of such compounds are known in the art, including those described in U.S. Pat. No. 4,598,044 to Kricka et al. and in Grundermann et al., Chemiluminescence in Organic Chemistry, Springer-Verlag, Berlin, 1987, pages 204–207.

Such compounds are generally known as "luminol-type hydrazides" and include phthalic hydrazides, naphthalene-1,2-dicarboxylic acid hydrazides, anthracene-2,3-dicarboxylic acid hydrazides, phenanthrene-1,2-dicarboxylic acid hydrazides, fluorene-1,2-dicarboxylic acid hydrazides, benzo[g,h,i]-perylene-1,2-dicarboxylic acid hydrazides, coronene-1,2-dicarboxylic acid hydrazides, and others readily apparent to one skilled in the art.

In particular, the DPD's that can be employed in the instant invention are defined by the following structural formula:

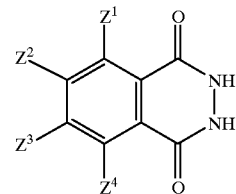

wherein $Z^1$, $Z^2$, $Z^3$, and $Z^4$ are independently hydrogen; an alkyl containing from about 1 to about 6 carbon atoms such as methyl, ethyl, isopropyl, t-butyl, sec-pentyl and hexyl; an alkenyl containing from about 2 to about 6 carbon atoms such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl; a hydroxy; an alkoxy containing from about 1 to about 6 carbon atoms such as methoxy, ethoxy, isopropoxy, t-butoxy and hexoxy; a carboxy; an amino including amino substituted with alkyl or alkanoyl, such as methylamino, ethylamino; amido (for example, acetamido and hexanamido); dimethylamino, diethylamino and diisobutylamino; a conjugated aminoalkenyl (for example, as defined below); or an aminoaryl including substituted aminoaryl, such as p-(N,N-dimethylamino)phenyl, p-(N,N-diethylamino)phenyl and 5-amino-2,3-dihydro-1,4-phthalazinedione-8-yl (also known as luminyl).

At least one of $Z^1$ and $Z^2$ is an amino (including substituted amino, as defined above), conjugated aminoalkenyl (including substituted aminoalkenyl as described above) or an aminoaryl such as p-(N,N-dimethylamino)-phenyl, p-(N,N-diethylamino)phenyl and 5-amino-2,3-dihydro-1,4-phthalazinedione-8-yl. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group such as 2-(N,N-diisopropylamino)vinyl, 2-(N,N-diisobutylamino)vinyl and 2-(N,N-diisopentylamino)-vinyl; and dialkylaminobutadienyl groups, such as 4(-N,N-diethylamino)-1,3-butadiene-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or an alkoxy having from about 1 to about 4 carbon atoms such as methoxy, ethoxy and isopropoxy. Preferably, such fused rings are substituted with one or more primary, secondary or tertiary amines, hydroxy or alkoxy as described above.

Representative useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol (5-amino-2,3-dihydro-1,4-phthalazinedione) and isoluminol (6-amino-2,3-dihydro-1,4-phthalazinedione) are preferred, and luminol is most preferred.

Other useful classes of DPD compounds are described in the Gundermann et al. publication cited above, and include substituted or unsubstituted phthalic acid hydrazides, anthracene-2,3-dicarboxylic acid hydrazides, phenanthrene dicarboxylic acid hydrazides, fluorene-1,2-dicarboxylic acid hydrazides, benzo[g,h,i]perylene-1,2-dicarboxylic acid hydrazides and coronene-1,2-dicarboxylic acid hydrazides, such as those illustrated by the following structures:

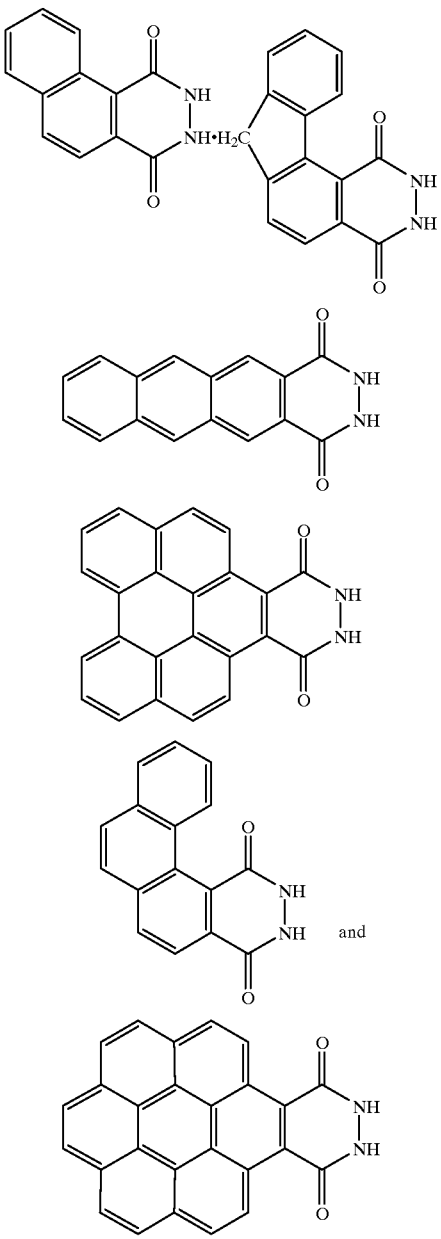

Other phthalazinedione analogs recognized by those skilled in the art as being useful in this invention include those disclosed in European Patent Application No. 91310875.9 to Masuya et al. and U.S. Pat. No. 5,324,835 to Yamaguchi, the contents of which are incorporated herein by reference.

The compounds identified above can be obtained commercially, or be prepared using conventional starting materials and procedures well known to those skilled in the art.

The second component of the wash composition employed in the instant invention is a halogen, pseudohalogen, halogen-providing source or pseudohalogen-providing source. The terms "halogen or halogen-providing source" as used herein denote any material which when added to the wash composition of the instant invention provides a halogen anion, i.e. a fluoride, chloride, bromide or iodide anion. This includes the halogens like chloride, bromide and iodide. The halogen providing source may comprise a metal or non-metal halogen salt. Non-metal salts include, but are not limited to, ammonium, alkylammonium, substituted alkylammonium, arylammonium, substituted arylammonium, hydrazinium, oxonium, tropylium, sulfonium and the like. The halogen-providing source may also be a polymeric material comprising a homopolymer or copolymer containing any combination of the above cationic species with a halogen as a counter-ion. An example of such a material is $NH_4Br$. Typically, the halogen-providing source is added to the composition as a Group IA metal salt. Other metal salts besides Group IA-containing metals are also contemplated herein. In a highly preferred embodiment of the instant invention, the halogen-providing source is NaBr.

The terms "pseudohalogen or pseudohalogen-providing source" are used herein to denote any material which when added to the composition employed in the instant invention provides anions which have a high electron affinity that is comparable to the halogens. It should be noted that the pseudohalogen-providing source is typically, but not limited to, a Group IA metal compound. The pseudohalogen or pseudohalogen-providing source may be a metal or non-metal compound as described above for halogen-providing sources, as for example, ammonium, alkylammonium and etc. and polymers thereof. Suitable pseudohalogens that may be present in the analytical signal-providing composition include, but are not limited to, $CN^-$, $SCN^-$, $OCN^-$, azide, isonitrile and the like. Of the pseudohalogens, $SCN^-$is particularly preferred. A preferred pseudohalogen-providing source employed in the instant invention is NaSCN.

The third component of the wash composition employed in the instant invention is a peroxide or a peroxide-generating reagent composition. The term 'peroxide' includes inorganic or organic peroxide compounds that are typically employed in the prior art. By peroxide-generating reagent composition, it is meant to include any reagent composition which is capable of producing peroxide when added to the signal-providing composition employed in the instant invention. Such peroxide-generating reagent compositions are well known to those skilled in this art and include, but are not limited to, perborates, peracetates, urea peroxide, and organic peroxides such as peracids, peroxybenzoic acid and oxones as well as hydroperoxides.

The wash composition employed in the present invention is generally buffered to a pH of from about 6.5 to about 10, more preferably from about 6.8 to about 8.0, using one or more suitable biological buffers having a pKa of about 6.0 to about 8.0. These buffers are well known in the art. Illustrative examples of such buffers include, but are not limited to, Tris(hydroxymethyl)aminomethane-HCl (Tris- HCl); 2-[N-morpholino]ethanesulfonic acid (MES); Piperazine-N,N'-bis [2-ethanesulfonic acid] (PIPES); 3-[N-Morpholino]-2-hydroxypropanesulfonic acid (MOPSO), phosphate buffers and the like. of the biological buffers mentioned above, Tris-HCl is particularly preferred.

In the wash composition employed in the present invention, the amounts of each component may vary depending upon its intended use, the particular sensitivity of the reagents and other factors well understood by one skilled in the art. Thus, the following general ranges are meant to provide guidance for the skilled worker, and not to limit the practice of the invention.

Specifically, the amount of buffer employed in the present invention is readily apparent to one skilled in the art since it is well known how to determine the quantity of any buffer needed to maintain a desired pH. The amount of signal-generating compound, DPD, is generally at least about 0.01 mMolar, with an amount in the range of from about 0.1 to about 10 mMolar being preferred.

In regard to the second component, i.e. the halogen, pseudohalogen, halogen-providing source or pseudohalogen-providing source, it is normally present in an amount of at least about 0.1 mMolar. More preferably, the halogen, pseudohalogen, halogen-providing source or pseudohalogen-providing source is present in the signal-providing composition in an amount of about 50 to about 100 mMolar.

Regarding the third component, i.e. the peroxide or peroxide-generating reagent composition, that component is present in the wash composition in an amount of at least about 0.02 mMolar. More preferably, the peroxide or peroxide-generating reagent composition is present in an amount of from about 0.5 mMolar to about 1.0 mMolar.

The element of the present invention can be used in a variety of assay formats to provide chemiluminescent signal in response to the reacted or unreacted form of the vanadium bromoperoxidase-labeled immunoreactant.

The following examples are given to illustrate the scope of this invention. Because these examples are given for illustrative purposes only, the invention embodied therein should not be limited thereto.

Except where noted, all reagents and equipment were obtained from Eastman Kodak Company or other commercial sources.

EXAMPLE 1

Preparation of an Aqueous Chemiluminescent Composition and a Vanadium Bromoperoxidase Solution An aqueous composition for providing a chemiluminescent signal was prepared as follows:

A buffer solution (pH 8.0) was prepared containing 100 $\mu$M of diethylenetriaminepentaacetic acid (DTPA), 0.75 M NaBr and 1% cetyltrimethylammonium bromide (CTAB) in a 0.05 M Tris-HCl buffer.

The signal-providing composition was prepared from a two-part mixture. The first part contained 1 mM of Na luminol and the second part contained 1 mM $H_2O_2$, both of which were prepared in the above buffer. These two parts were combined immediately before use.

A vanadium bromoperoxidase (from Ascophylum nodosum) stock solution stored at 4° C. was serially diluted in 0.05 M Tris-HCl, pH 8, and 0.01% bovine serum albumin (BSA) to provide a known concentration of the vanadium bromoperoxidase ranging from 10 to 50,000 attomoles.

A coated element was then prepared having the following reagent matrix composition:

| | |
|---|---|
| Bead Spread Layer: | 0.1 M Tris, pH 8.0 |
| | Polymeric beads (VtE) |
| | Binder (MaWnaMt) |
| | 0.5 g/m$^2$ TSH Ab beads |
| | DTPA (10$^{-4}$ M) |
| Gel Pad: | Gelatin |
| | 0.2 M Tris pH 8.0 |
| | DTPA (10$^{-4}$ M) |
| | TX-100 |
| | Hardener (BVSME) |
| Support: | 7 mil Estar (polyethylene terephthlate) |

The following definitions apply to the above reagent matrix:
Tris: Tris(hydroxymethyl)amino-methane buffer.
Polymeric beads: Poly(vinyltoluene-co-mehtacrylic acid beads).
Binder: Poly(methyl acrylate-co-sodium 2-acrylamido-2-methyl-propanesulfonate-co-2-acetoacetoxyethyl methacrylate).
TSH Ab beads: poly(styrene-co-3-(p-vinylbenzylthio) propanoic acid) having covalently attached an antibody against thyroid stimulating hormone (TSH).
TX-100: Triton X-100, an octylphenoxy polyethoxy ethanol surfactant sold by Rohm and Haas Co.
BVSME: Bis(vinylsulfonyl)methyl ether.
MaWnaMt=poly(methyl acrylate-co-2-acrylamido-2-methyl propane sulfonic acid, sodium salt-co-acetoacetoxyethylmethacrylate) (90/4/6).
Evaluation of Vanadium Bromoperoxidase for Chemiluminescent Signal on a Sensitive Detection Immunoassay Coating The above prepared chemiluminescent signal-providing composition and vanadium bromoperoxidase buffered solutions were used as follows:

An element in the form of a slide was assembled by placing a 16 mm$^2$ section of the above prepared coating on an EKTACHEM (trademark) C-Slide base (as described in U.S. Ser. No. 938,460 to Belly et al. earlier referenced). A Whatman GF/B absorbent microfiber glass material (Whatman Specialty Products Division, Product No. PD 008-12A-100) with a 10 mm diameter centered hole to enable a sample application, was positioned over the coating. An impervious annular plastic top-piece was then placed on the absorbent layer and the entire assembly was sealed with tape (For complete assembly details see FIGS. 1 and 2 of U.S. Ser. No. 938,460 to Belly et al.).

The element was then washed with 100 $\mu$l of the above described chemiluminescent signal-providing composition at a rate of 1 $\mu$l/sec. Following the application of the wash solution, the appropriate dilution of vanadium bromoperoxidase described above in 5 $\mu$l of the chemiluminescent signal-providing composition was spotted onto the coating. The element was immediately disassembled and the chemiluminescent signal of the coating was measured using a TURNER (trademark) TD-20e luminometer at ambient temperature. The luminometer was modified to accommodate the disassembled 16 mm$^2$ coating by use of an adapter that permitted read out of the central 10 mm diameter portion the coating.

FIG. 1 shows the chemiluminescent output (10 sec. integral at t=4 minutes after placement in the modified luminometer) under the above conditions for this assay. More specifically, FIG. 1 shows that the element of the instant invention produces an absolute signal which is easily detectable like that of the prior art element.

In FIG. 1 the control element contains horseradish peroxidase as a signal-generating enzyme, and 3'-chloro-4'-hydroxyacetanilide as an enhancer in the wash composition as described in U.S. Pat. No. 5,372,931 to Friedman et al., wherein the wash composition was modified as follows: 0.05 M Tris-HCl, pH 8.0, 0.1% cetyltrimethyl ammonium chloride (CTAC), 150 μM 3'-chloro-4'-hydroxyacetanilide in addition to stated components therein.

FIG. 2 shows the signal-to-noise ratio, a recognized measure of system sensitivity to those skilled in the art. The data in FIG. 2 were obtained using the element of the present invention and a control element which contained horseradish peroxidase as a signal-generating enzyme. The wash composition for the HRP control included 3'-chloro-4'-hydroxyacetanilide as an enhancer as described in U.S. Pat. No. 5,372,931 to Friedman et al., modified as follows: 0.05 M Tris-HCl, pH 8.0, 0.1% cetyltrimethyl ammonium chloride (CTAC), 150 μM 3'-chloro-4'-hydroxyacetanilide in addition to stated components therein. This figure shows that the element of the present invention provides greater sensitivity than the control element.

EXAMPLE 2
Comparison of Element Stability

This example compares the stability of vanadium bromoperoxidase in a dry element to that of HRP in a dry element. A base coated element was prepared having the following reagent matrix composition coated on a 7 mil Estar (polyethylene terepthalate) support:

| LAYER | COMPONENT | LAYDOWN (g/m$^2$) |
| --- | --- | --- |
| Porous Spread Layer | Polymer Beads-VtE | 130 |
| | Latex Binder-MaWnaMt | 2.583 |
| | Buffer-TES | 0.219 |
| Subbing (Receptor) | Copolymer-IMnAg(85/5/10 | 0.50 |
| | Buffer-TES | 0.10 |
| | Surfactant-TX-100 | 0.02 |
| First Reagent | Matrix-Gelatin | 10.0 |
| | Buffer-TES | 4.58 |
| | Surfactant-TX-100 | 0.02 |
| | Hardener-BVSME | 0.150 |

KEY:
VtE = poly(vinyltoluene-co-methacrylic acid) (98/2)
MaWnaMt = poly(methyl acrylate-co-2-acrylamido-2-methyl propane sulfonic acid, sodium salt-co-acetoacetoxyethylmethacrylate) (90/4/6)
TEL = N-[2-Hydroxy-1,1-bis(hydroxymethyl)ethyl]taurine
BVSME = Bis(vinylsulfonyl)methyl ether
IMnAg = poly(N-isopropylacrylamide-co-2-hydroxyethylmethacrylate-co-methylenebisacrylamide) (85/5/10).

The same reagents as described in Example 1 for vanadium bromoperoxidase stock solution were employed in this example except that the vanadium bromoperoxidase and HRP stock solutions were diluted to $10^{-8}$ M in a 10 mM phosphate buffer, pH 7.0.

Both elements were assembled using the procedure described in Example 1 except the absorbent material was not included in the slide assembly. Then, 10 μl of either the above vanadium bromoperoxidase or the above HRP stock solutions were spotted on the elements.

Each element was then aged in the dark at room temperature for 30 minutes, 2, 4, 6, 24 and 48 hours. After each interval, the element was cut to remove the coating material which was then extracted in 1 ml of a buffer containing phosphate (pH 7.0), 0.15 M NaCl and 0.1% BSA. The extracted material was then centrifuged for about 2 minutes to separate the particulate and solid materials.

The measurement of enzyme activity was accomplished by the addition of 200 μL of the appropriate signal-generating solution to 10 μL of the extracted supernatant. For the vanadium bromoperoxidase, the signal-providing wash composition of the instant invention was used. For HRP, the reagent composition disclosed in Example 1 of U.S. Pat. No. 5,372,931 to Friedman et al. was used. The chemiluminescent signal was then determined using a DYNATECH (trademark) ML3000 luminometer at 37° C.

The results of these experiments are shown graphically in FIG. 3 (1.0 sec. integral, at t=5 min. for each interval point). FIGS. 4(a) and (b) are plots of the data from FIG. 3 depicting percent remaining activity of (a) HRP and (b) vanadium bromoperoxidase. Specifically, these figures clearly show that the stability of the vanadium bromoperoxidase-containing element remains essentially constant over a long period of time (up to 48 hours). In contrast, a dramatic decrease in the HRP-containing element is clearly shown.

The above experiments and examples are given to illustrate the scope and spirit of the present invention. These embodiments and examples will make apparent to those skilled in the art, other embodiments and examples. These other embodiments and examples are within the contemplation of the present invention; therefor, the instant invention should be limited only by the appended claims.

What is claimed is:

1. A method for the determination of a specific binding ligand comprising:
    (A) contacting a fluid sample suspected of containing said specific binding ligand with an analytic element comprising:
        (i) a porous spreading zone, and
        (ii) at least one additional zone which is in fluid contact with said porous spreading zone, said element containing in at least one of said zones a vanadium bromoperoxidase-labeled ligand or ligand analog, and in a separate zone, an immobilized receptor that binds said ligand or ligand analog;
    (B) applying a wash solution to said element to bring about a separation of free vanadium bromoperoxidase-labeled ligand or ligand analog from vanadium bromoperoxidase-labeled ligand or ligand analog that is bound to said immobilized receptor, said wash solution comprising a composition having a pH of from about 6.5 to about 10, wherein said composition comprises:
        (a) a chemiluminescent signal-generating reagent which provides a signal in response to the catalytic activity of said vanadium bromoperoxidase, wherein said signal-generating reagent is a 2,3-dihydro-1,4-phthalazinedione derivative;
        (b) a halogen, pseudohalogen, halogen-providing source or pseudohalogen-providing source; and
        (c) a peroxide or a peroxide-generating reagent composition, and
    (C) detecting either the free or bound vanadium bromoperoxidase labeled ligand or ligand analog as a measure of said specific binding ligand.

2. The method of claim 1 wherein said vanadium bromoperoxidase is obtained from *Ascophyllum nodosum, Ceramirum rubrum, Laminaria saccharina, Fucus distichus, Corallina pilulifera, Corallina officinals* or *Macrocystis pyrifera*.

3. The method of claim 2 wherein said vanadium bromoperoxidase is obtained from *Ascophyllum nodosum*.

4. The method of claim, 1 wherein said 2,3-dihydro-1,4-phthalazinedione derivative is luminol, isoluminol, N-(4- aminobutyl)-N-ethylisoluminol hemisuccinimide, N-(6-amino-hexyl)-N-ethylisoluminol, N-ethylisoluminol or 7-dimethylaminonaphthalene-1,2-dicarboxylic acid.

5. The method of claim 4 wherein said 2,3-dihydro-1,4-phthalazinedione is luminol.

6. The method of claim, 1 wherein said halogen-providing source is a metal or a non-metal salt.

7. The method of claim 6 wherein said halogen-providing source is NaBr.

8. The method of claim 1 wherein said pseudohalogen-providing source is a metal or non-metal compound containing as one of its ligands CN⁻, SCN⁻, OCN⁻, azide or isonitrile.

9. The method of claim 8 wherein said pseduohalogen is SCN⁻.

10. The method of claim 1 wherein said peroxide-generating reagent is a perborate, peracetate, urea peroxide, peroxybenzoic acid, peracid, oxone or a hydroperoxide.

11. The method of claim 1 wherein said peroxide is hydrogen peroxide.

12. The method of claim 1 further comprising (iii) an absorbent material in fluid contact with one or more of said zones.

13. The method of claim 1 wherein said vanadium bromoperoxidase is obtained from *Ascophyllum nodosum*, said 2,3-dihydro-1,4-phthalazinedione derivative is luminol, said halogen-providing source is NaBr and said peroxide is hydrogen peroxide.

14. The method of claim 1 wherein said vanadium bromoperoxidase is obtained from *Ascophyllum nodosum*, said 2,3-dihydro-1,4-phthalazinedione derivative is luminol, said pseudohalogen-providing source NaSCN and said peroxide is hydrogen peroxide.

15. The method of claim 1 wherein the the pH of the wash solution is in the range of about pH 8 to about pH 10.

16. A method for the determination of a specific binding ligand comprising:
(A) contacting a fluid sample suspected of containing the specific binding ligand with an analytic element comprising:
(i) a porous spreading zone, and
(ii) at least one additional zone which is in fluid contact with the porous spreading zone, the element containing in at least one of the zones an immobilized receptor that binds the ligand and in the same zone or a separate zone or zones a vanadium bromoperoxidase-labeled receptor that binds the ligand, thereby forming a complex of immobilized receptor, vanadium bromoperoxidase-labeled receptor and ligand;
(B) applying a wash solution to the element to bring about a separation of free vanadium bromoperoxidase-labeled receptor from vanadium bromoperoxidase-labeled receptor in said complex, the wash solution comprising a composition having a pH in the range of about pH 6.5 to about pH 10, wherein the composition comprises:
(a) a chemiluminescent signal-generating reagent which provides a signal in response to the catalytic activity of the vanadium bromoperoxidase, wherein the signal-generating reagent is a 2,3-dihydro-1,4-phthalazinedione derivative;
(b) a halogen, pseudohalogen, halogen-providing source or pseudohalogen-providing source; and
(c) a peroxide or a peroxide-generating reagent composition, and
(C) detecting either the free vanadium bromoperoxidase-labeled receptor or the vanadium bromoperoxidase-labeled receptor in said complex as a measure of the specific binding ligand.

17. The method of claim 16 wherein the the pH of the wash solution is in the range of about pH 8 to about pH 10.

18. The method of claim 16 wherein said vanadium bromoperoxidase is obtained from *Ascophyllum nodosum, Ceramirum rubrum, Laminaria saccharina, Fucus distichus, Corallina pilulifera, Corallina officinals* or *Macrocystis pyrifera*.

19. The method of claim 16 wherein said vanadium bromoperoxidase is obtained from *Ascophyllum nodosum*.

20. The method of claim 16 wherein said 2,3-dihydro-1,4-phthalazinedione derivative is luminol, isoluminol, N-(4-aminobutyl)-N-ethylisoluminol hemisuccinimide, N-(6-amino-hexyl)-N-ethylisoluminol, N-ethylisoluminol or 7-dimethylaminonaphthalene-1,2-dicarboxylic acid.

21. The method of claim 20 wherein said 2,3-dihydro-1,4-phthalazinedione is luminol.

22. The method of claim 16 wherein said halogen-providing source is a metal or a non-metal salt.

23. The method of claim 22 wherein said halogen-providing source is NaBr.

24. The method of claim 16 wherein said pseudohalogen-providing source is a metal or non-metal compound containing as one of its ligands CN⁻, SCN⁻, OCN⁻, azide or isonitrile.

25. The method of claim 24 wherein said pseudohalogen is SCN⁻.

26. The method of claim 16 wherein said peroxide-generating reagent is a perborate, peracetate, urea peroxide, peroxybenzoic acid, peracid, oxone or a hydroperoxide.

27. The method of claim 26 wherein said peroxide is hydrogen peroxide.

28. The method of claim 16 wherein the element further comprises (iii) an absorbent material in fluid contact with one or more of said zones.

29. The method of claim 16 wherein said vanadium bromoperoxidase is obtained from *Ascophyllum nodosum*, said 2,3-dihydro-1,4-phthalazinedione derivative is luminol, said halogen-providing source is NaBr and said peroxide is hydrogen peroxide.

30. The method of claim 16 wherein said vanadium bromoperoxidase is obtained from *Ascophyllum nodosum*, said 2,3-dihydro- 1,4-phthalazinedione derivative is luminol, said pseudohalogen-providing source NaSCN and said peroxide is hydrogen peroxide.

\* \* \* \* \*